United States Patent [19]

Burks et al.

[11] 4,086,917
[45] May 2, 1978

[54] FETAL HEART RATE MONITORING SYSTEM

[75] Inventors: Nathaniel W. Burks, San Diego; Newton E. Ball, Solana Beach; David L. Britt, San Diego, all of Calif.

[73] Assignee: Medical Instruments & Technology Corp., San Diego, Calif.

[21] Appl. No.: 654,275

[22] Filed: Feb. 2, 1976

Related U.S. Application Data

[63] Continuation of Ser. No. 449,251, Mar. 8, 1974, abandoned.

[51] Int. Cl.² ............................................. A61B 5/02
[52] U.S. Cl. ........................... 128/2.05 T; 128/2.05 Z
[58] Field of Search ...................... 128/2.05 P, 25.0 R, 128/25.0 T, 2.05 Z, 2.06 A, 2.06 B, 2.06 E, 2.06 F, 2.06 R, 2.1 A, 2.1 R; 174/48, 49; 317/101 CB

[56] References Cited

U.S. PATENT DOCUMENTS

| | | | |
|---|---|---|---|
| 3,212,496 | 10/1965 | Preston | 128/2.1 A |
| 3,561,430 | 2/1971 | Filler, Jr. et al. | 128/2.05 T |
| 3,572,316 | 3/1971 | Vogelman et al. | 128/2.1 A |
| 3,612,041 | 10/1971 | Ragsdale | 128/2.06 A |
| 3,613,670 | 10/1971 | Edenhofer | 128/2.06 F |
| 3,710,199 | 1/1973 | Cignoni, Jr. | 317/101 CB |
| 3,799,147 | 3/1974 | Adolph et al. | 128/2.06 R |
| 3,859,984 | 1/1975 | Langley | 128/2.05 Z |
| 3,943,918 | 3/1976 | Lewis | 128/2.1 A |

FOREIGN PATENT DOCUMENTS

| 1,531,413 | 5/1968 | France | 128/2.06 R |
|---|---|---|---|

*Primary Examiner*—William E. Kamm
*Attorney, Agent, or Firm*—Ellsworth R. Roston

[57] ABSTRACT

Each ultrasonic transducer in a plurality provides a particular signal having characteristics related to the heart rate of an associated fetus. Each particular signal is processed in an associated labor room monitor and modulated on a different carrier frequency for transmission on power lines in the hospital. At a remote location, a nurses station power unit is modular with nurses station monitors. The line signals are individually demodulated in an associated one of the nurses station monitors to provide an indication of heart rate. Alternatively, the transducer assemblies can be coupled to delivery room monitors to provide an indication of heart rate.

The transducer assemblies are uniquely shielded to inhibit interference of spurious low frequency signals with the particular signals. The particular signals are partially detected in the transducer assemblies so that the assemblies can be used with both the labor room and delivery room monitors.

In the monitors, the particular signals are separated into signals each characterized by a particular fundamental frequency. A voting network elects to process that signal most indicative of the fetal heart rate.

Audio and video indications are provided to signal a heart rate beyond a preferred range and to signal a heart rate of substantially zero. If the transducer assembly becomes dislocated, the indicated zero heart rate activates means for storing the previous heart rate. When the assembly is relocated, the previous heart rate is used to avoid delay associated with regenerating heart rate information.

13 Claims, 9 Drawing Figures

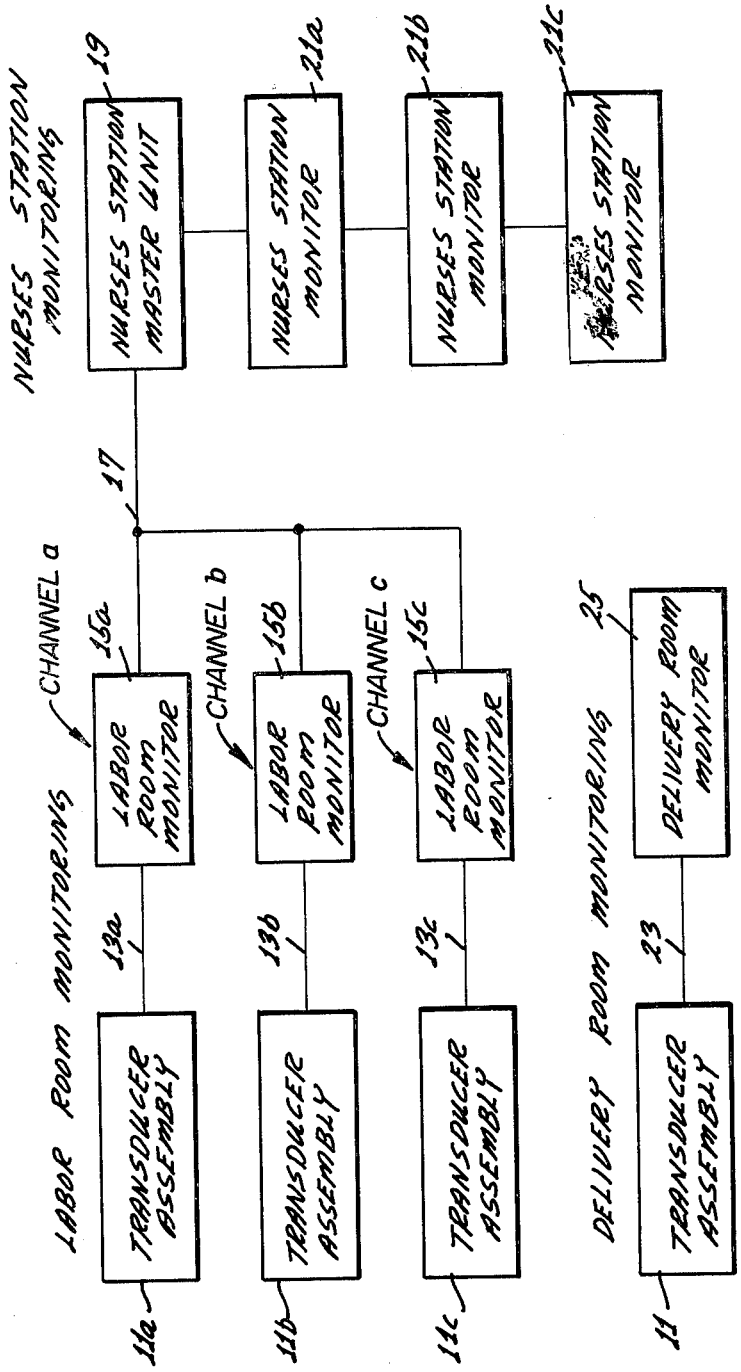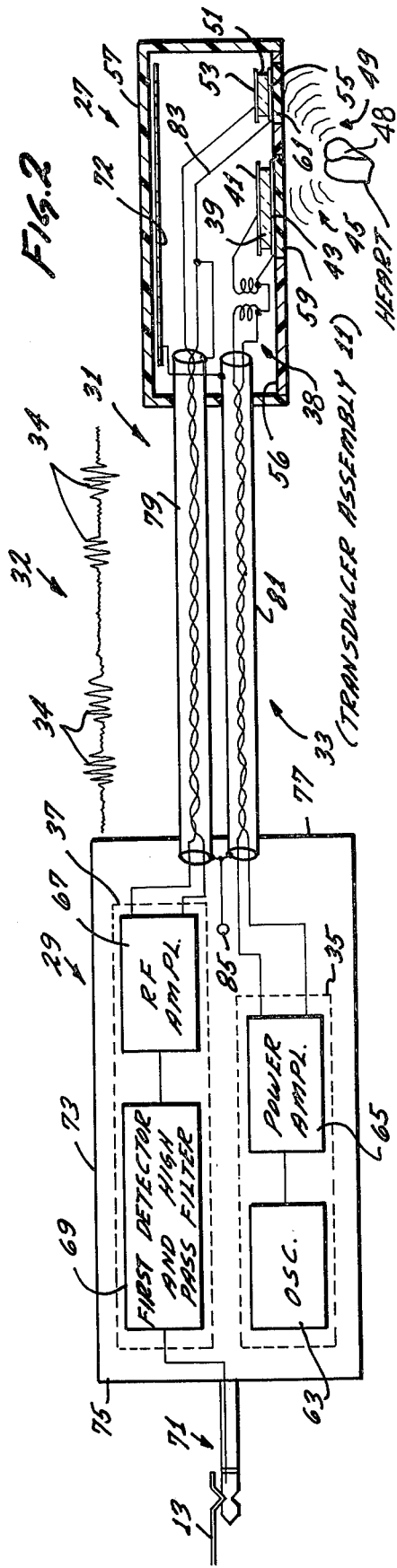

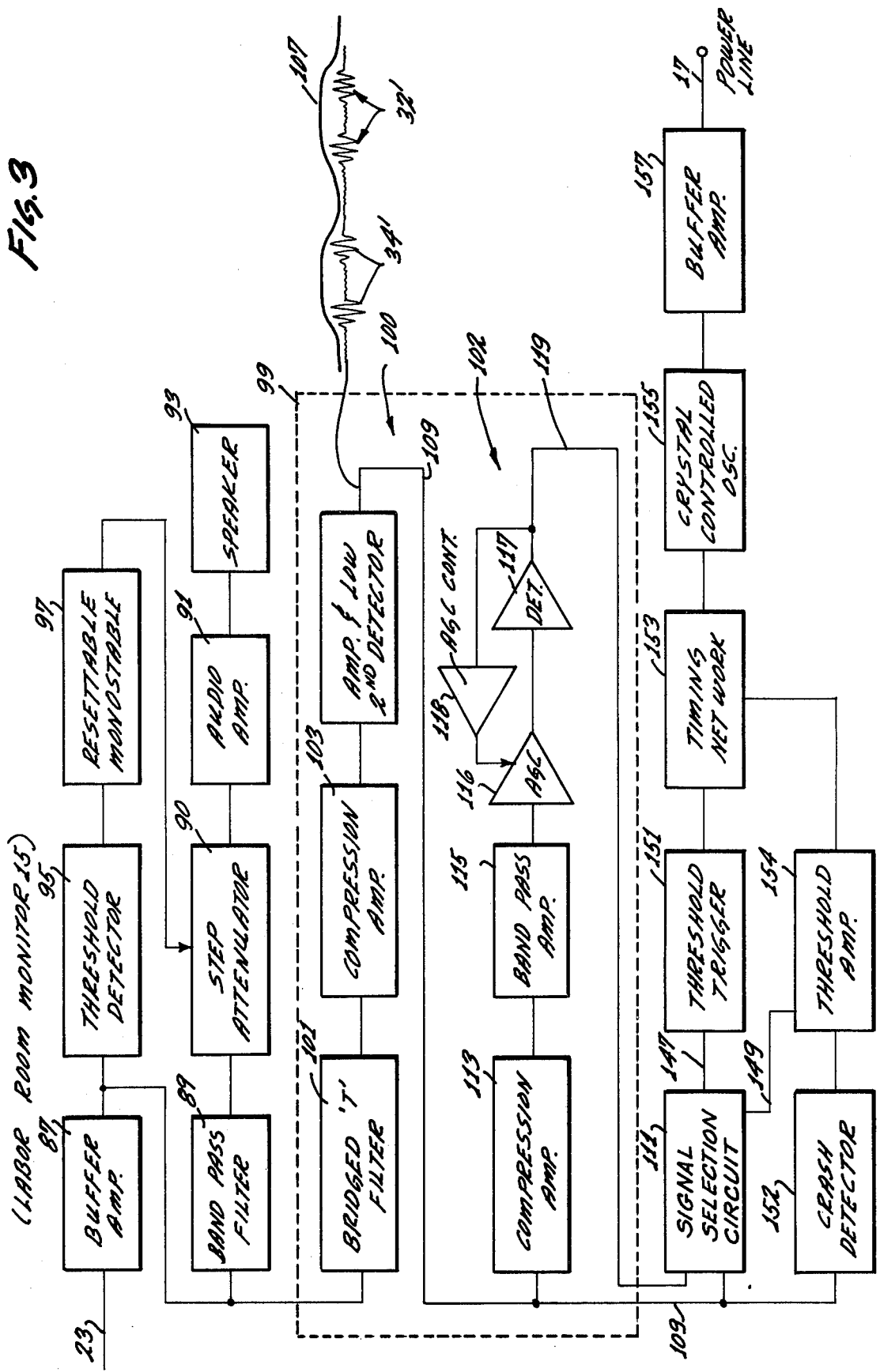

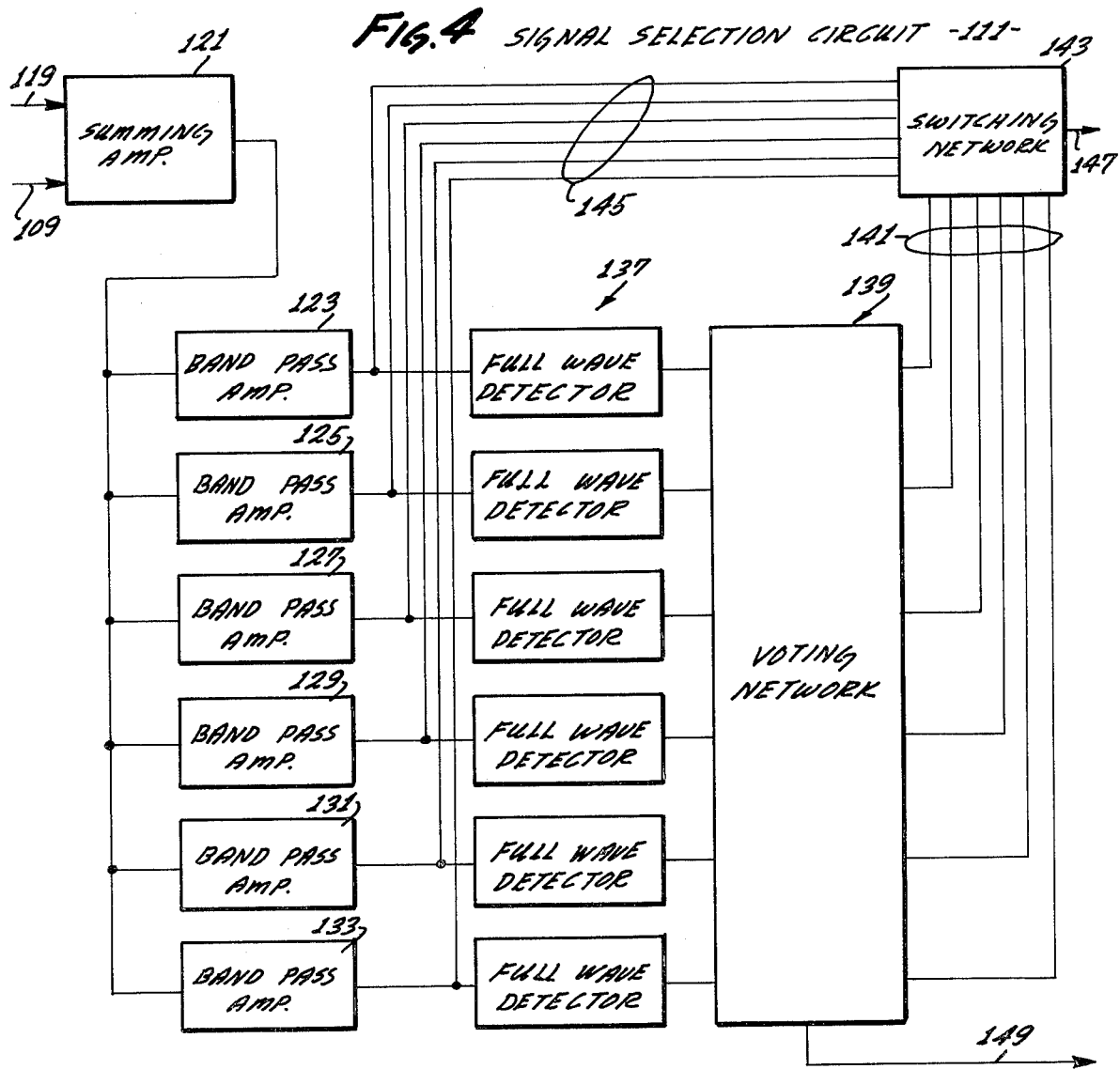
FIG. 4 SIGNAL SELECTION CIRCUIT -111-
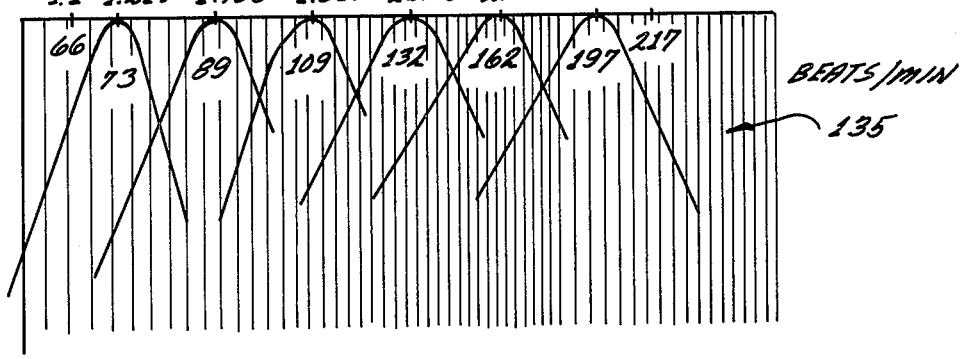
FIG. 5

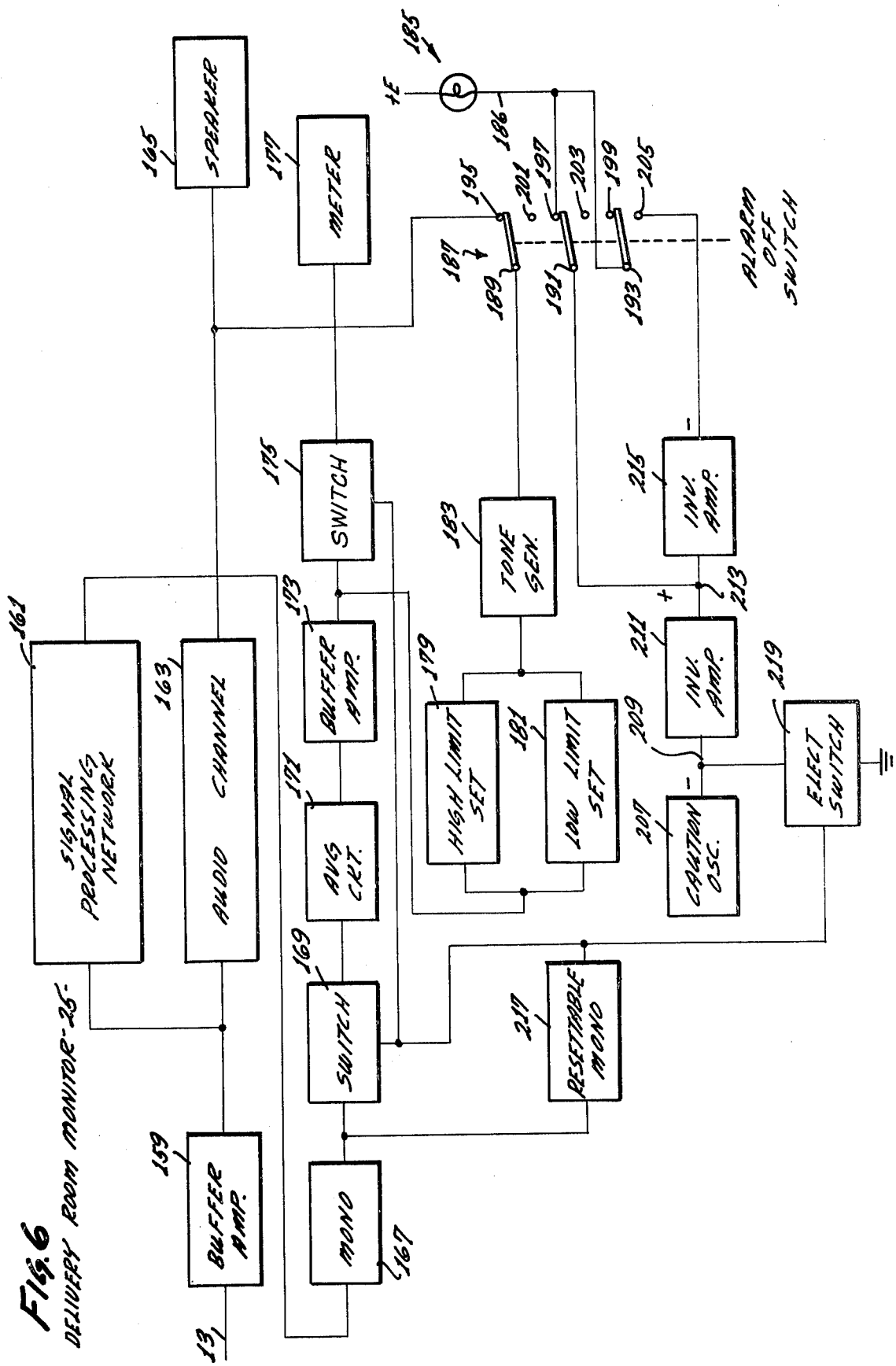

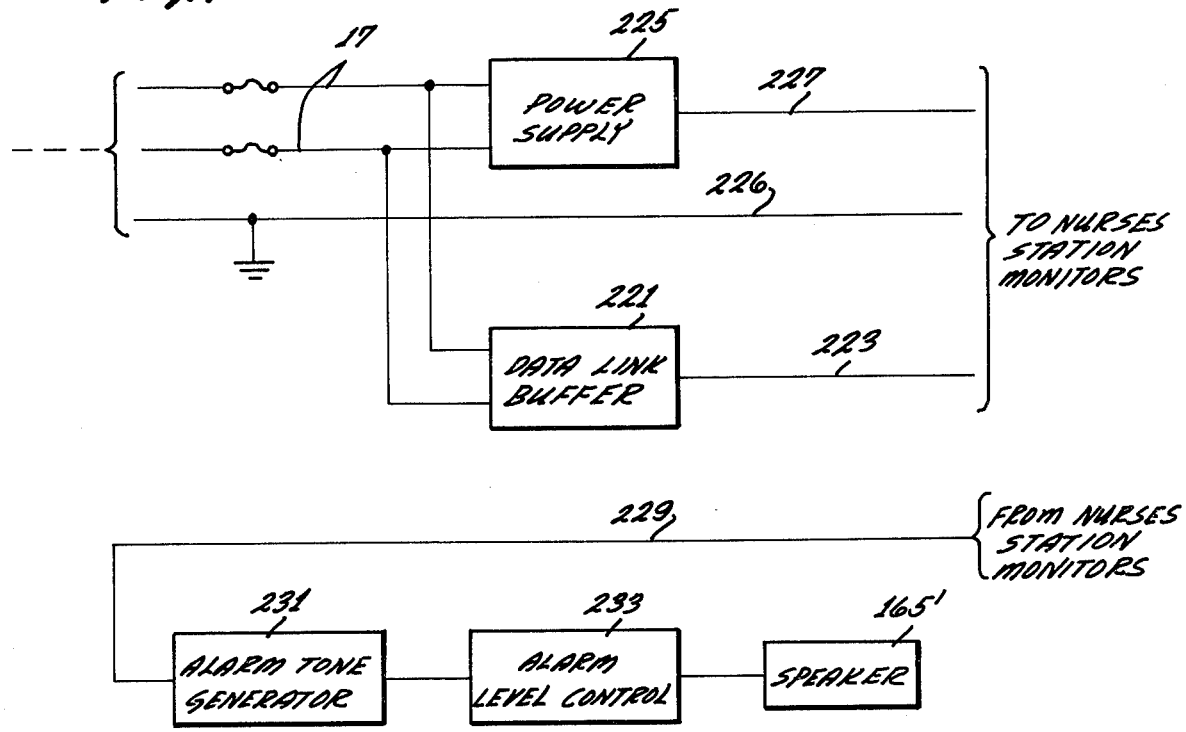
FIG. 7 NURSES STATION MASTER UNIT-19
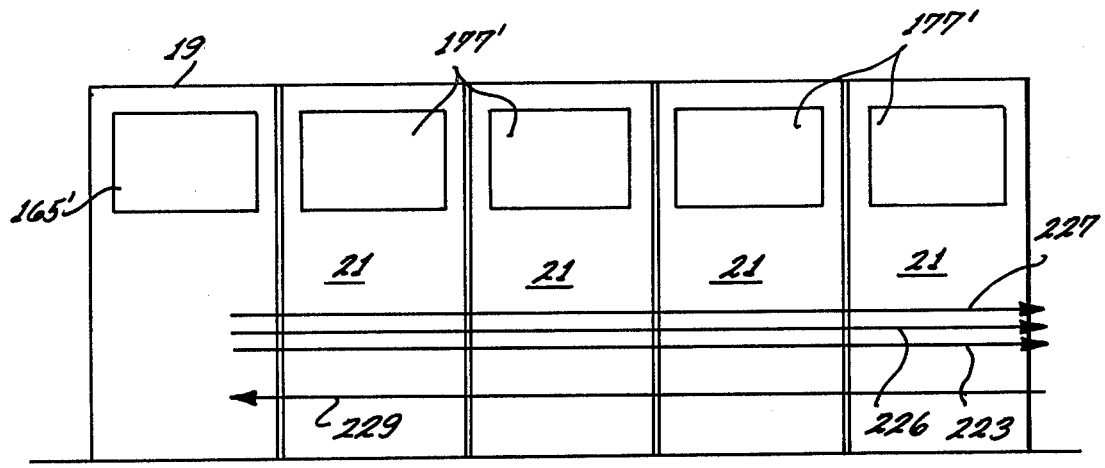
FIG. 8 NURSES STATION

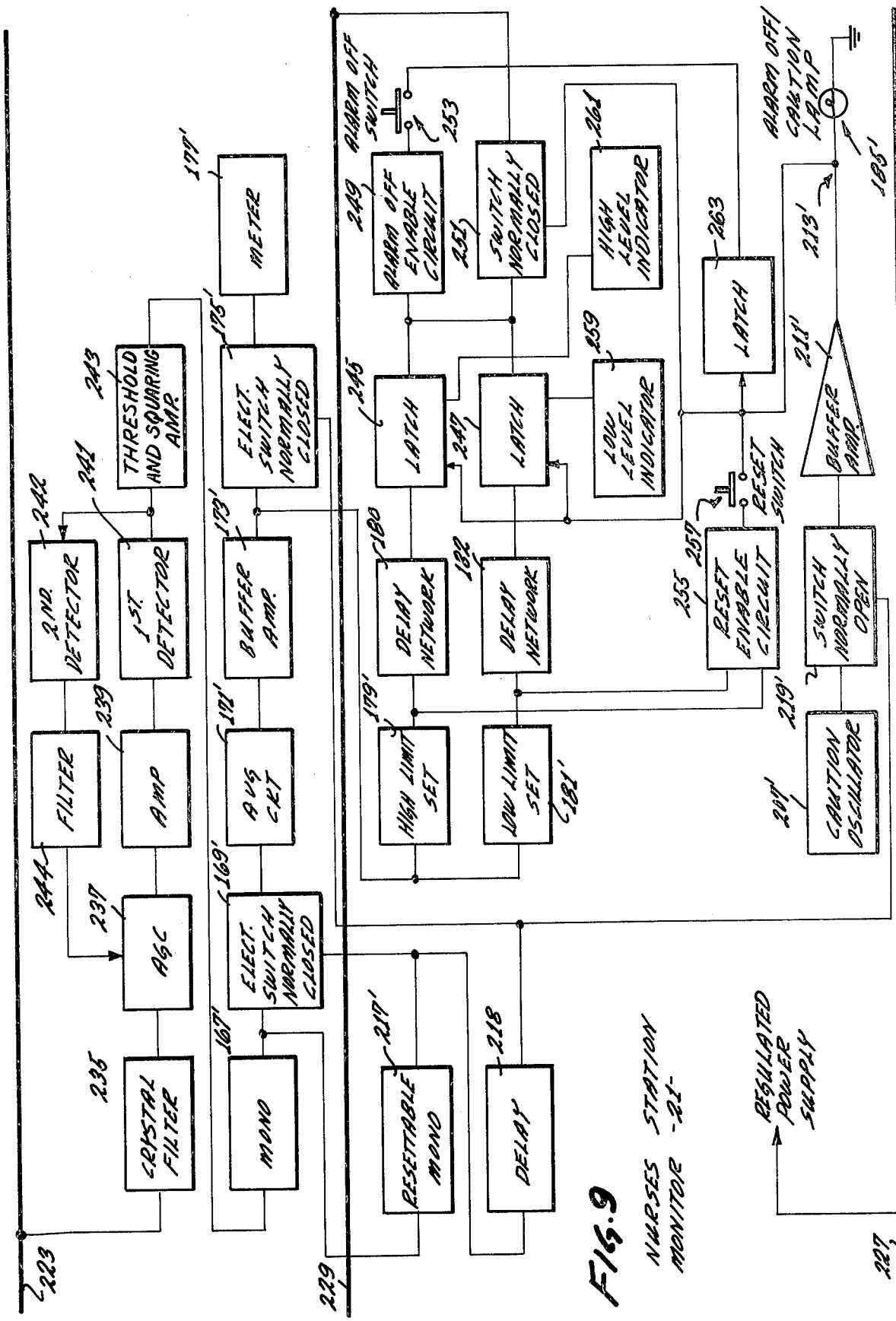

FETAL HEART RATE MONITORING SYSTEM

This is a continuation of application Ser. No. 449,251, filed Mar. 8, 1974, and now abandoned.

BACKGROUND OF THE INVENTION

1. Field of the Invention

This invention relates generally to apparatus for monitoring the heart rate of a fetus and more specifically to such apparatus adapted to transmit signals through hospital power lines or by direct wiring to a remote monitoring station.

2. Description of the Prior Art

In recent years medicine has made significant advances in many areas related to the care of mothers and their babies but the number of children born with brain damage has not decreased significantly. It is believed that in certain of these babies, the brain damage has occurred during labor or at birth due to a reduction in the supply of oxygen.

It has been found that by monitoring the fetus, doctors can be provided with a continuous and highly accurate report on the most widely used indicator of fetal condition, the fetal heart rate. By monitoring the fetal heart rate, doctors have been able to decrease the need for emergency Cesarean section. This decrease has been made possible by conservative measures such as changing the maternal position to relieve pressure on the umbilical cord.

Various apparatus have been used for monitoring the fetal heart rate. For example stethoscopes have been used to listen to the fetal heart beat. This particular means for monitoring the heart rate has been unsatisfactory during the periods of labor contractions due to the high degree of extraneous or artifact noise. Since fetal distress is apt to occur during labor contractions, the stethoscopic means for monitoring the heart rate have not provided a satisfactory indication of fetal condition.

The heart rate of the fetus has also been monitored using various electronic apparatus to determine certain characteristics of the heart beat. This is usally accomplished using two electrodes one of which is attached to the head of the fetus. Although this technique has provided reasonably accurate data, there are obvious disadvantages. For example, the electrode can not be attached to the head of the fetus until the cervix has opened sufficiently and the amniotic sack has been ruptured. For obvious reasons, this technique has not been used for monitoring the fetus in the early stages of labor. In addition the electrode has been applied either blindly or by using a special light source which requires special training. Furthermore, the presence of a doctor has been required to supervise the electrode attachment.

Ultrasonic transducers have also been used for monitoring the fetal heart rate. These transducers have transmitted an ultrasonic signal which has been reflected by the motion of tissue, such as the heart, to produce a Doppler effect and a corresponding electrical signal in the transducer. Since any movement of tissue within the path of the transmitted ultrasonic signal produces characteristics in the corresponding electrical signal, the particular characteristics associated with the heart beat are disguised in a high degree of extraneous or artifact noise.

The resulting electrical signal is of relatively low power and the characteristics of particular interest are of relatively low frequency. As a result, it has been particularly difficult to isolate these signals from the spurious low frequency signals in the atmosphere such as those transmitted by frequency modulated radio stations. Monitors of the prior art receiving these crude signals have been unable to satisfactorily separate the characteristics relating to the heart rate from the characteristics relating to the artifact noise and radio interference. As a consequence other types of sensors have typically been used in conjunction with the ultrasonic sensor to monitor the heart rate.

It has been desirable to monitor the fetal heart rate not only in the labor room and the delivery room but also at a remote location such as the nurses station. In some systems of the prior art, monitors have been provided in the labor room and hard wires have been run in the hospital walls between the labor room and the nurses station for each of the heart rates monitored. At the nurses station a single, self-contained unit has been used for each of the heart rates monitored.

The ultrasonic sensors, which have typically been attached to the abdomen of the mother with adhesive tape, have had a resonant frequency which has been matched by signal characterizing electronics in the receivers of the monitors. This matching has been desirable to maximize the power of the relatively crude signal received from the sensors. To facilitate the matching, each of the ultrasonic sensors has been designed for operation with a particular one of the monitors. As a consequence, when a mother has been removed from the labor room to the delivery room, the sensor associated with the labor room monitor has been removed and the sensor associated with the delivery room monitor has been attached. This procedure has been time consuming and the removal of the adhesive tape with the sensor has been particularly annoying to the mother.

At the nurses station, the monitors have included a meter providing an instantaneous indication of heart rate. Alarm means have provided an audible indication when the heart rate is above or below a preferred range of heart rates. When a nurse has been at the station and the alarm has sounded, it has been possible to read the meter to determine if the heart rate is high or low. In some cases, the nurse has been away from the station when the alarm has sounded, and the meter has returned to the preferred range prior to her return to the station. Although in some systems the alarm has remained active, there has been no indication as to whether the rate was higher or lower than the preferred range of heart rate.

When the ultrasonic sensor has become detached from the mother, the heart rate indication of substantially zero has provided the alarm indication. This detachment of the sensor has occurred quite frequently and the alarm has caused a high degree of concern when it was not particularly warranted. There has been no way to distinguish a heart rate of low level from a heart rate of substantial zero level.

When the sensor has first been attached, the heart rate has gradually built up to indicate a particular value. Each time the sensor has become disconnected, this undesirable gradual buildup has followed the reattachment. There has been no means for storing the particular value of the heart rate to avoid the gradual buildup of the rate signal following the reconnection of the sensor. In some systems, the interpulse period has been used to determine the heart rate. Although without averaging, this approach could provide an instantaneous indication of heart rate, the display would be very jumpy.

SUMMARY OF THE INVENTION

In the present invention, a labor room monitor, delivery room monitor, and nurses station monitor are each disclosed to have particular characteristics. An ultrasonic transducer assembly is shielded in a particular manner to inhibit the interference of spurious low frequency signals with the signals produced by the ultrasonic sensor.

The frequency characterizing electronics associated with the transmitter and receiver of the ultrasonic sensor are included in the transducer assembly. As a result, the highly desirable matching characteristics between the transmitter, receiver, and sensor are included in a single unit which is detachable from either the labor room monitor or the delivery room monitor. This is of particular advantage since a particular sensor need not be removed from the mother while she is moved from the labor room to the delivery room. Since the desirable matching characteristics are within the transducer assembly, these assemblies can be used interchangeably with any of the monitors in the hospital.

The labor room monitor is provided with characteristics for transmitting a signal through the house wiring of the hospital to a remote location such as the nurses station. Each of the heart rates monitored is modulated on a carrier of a different frequency so that a single phase of the house wiring can carry several channels between the labor room and the nurses station.

At the nurses station, a master unit provides power for several monitors each responsive to one of the carrier frequencies to detect the heart rate of one of the fetuses. Each of the monitors has characteristics for generating an alarm signal, and these signals can be introduced on a bus to activate a single alarm in the master unit. This modular construction has significantly reduced the size of the apparatus used to monitor several heart rates.

The modules at the nurses station have been provided with both low and high indicators so that a nurse responding to an alarm condition can ascertain if the heart rate was low or high without reference to the meter which might have returned to the preferred range of heart rates.

If the sensor assembly becomes displaced from the mother to provide a heart rate indication of substantially zero, the present invention is provided with means for storing a quantity related to the preceding heart rate value so that when the sensor assembly is reconnected there is no delay associated with the buildup of an integration circuit. This quantity is introduced directly to the meter to provide a jump in the heart rate indication, from zero to the stored level.

In each of the monitors of the present invention, separate alarm means is provided to distinguish a heart rate of low level from a heart rate of substantially zero level. Since the low fetal heart rate is typically associated with fetal distress, this alarm is provided with an audible indication. Since the heart rate of substantially zero level is associated with a disconnected sensor assembly, the associated alarm may provide merely a visual indication.

Each of the monitors can be provided with a detection circuit including a signal selection circuit having a plurality of filters and a voting network associated with each of the filters. Each of the voting networks votes in favor of the reproduction of its particular signal in accordance with the magnitude of its signal. Some of the voting networks vote against other signals whose magnitudes might be influenced by harmonics of the associated signal. The signal having the highest vote is assumed to include the particular heart rate information and is therefore reproduced. This selection circuit significantly reduces the influence of artifact noise in the signal from the ultrasonic sensor.

These and other features and advantages of the present invention will become more apparent with a description of the preferred embodiments with reference to the associated drawings.

DESCRIPTION OF THE DRAWINGS

FIG. 1 is a block diagram of one embodiment of the fetal heart rate monitoring system of the present invention including transducer assemblies, labor room monitors, a nurses station master unit, nurses station monitors, and a delivery room monitor;

FIG. 2 is a cross-sectional view of a sensor assembly, and a block diagram view of a signal characterizing network of the transducer assembly illustrated in FIG. 1;

FIG. 3 is a block diagram of one of the labor room monitors illustrated in FIG. 1 which includes a signal selection circuit;

FIG. 4 is a block diagram of one embodiment of the signal selection circuit illustrated in FIG. 3 which includes a voting network;

FIG. 5 is a graph illustrating a particular frequency spectrum of interest in the signal selection circuit of FIG. 3 and particular portions of the spectrum which are associated with the bandpass amplifiers of FIG. 4;

FIG. 6 is a block diagram of one embodiment of the delivery room monitor illustrated in FIG. 1;

FIG. 7 is a block diagram of one embodiment of the nurses station master unit illustrated in FIG. 1;

FIG. 8 is a front elevational view of the nurses station master unit coupled to several nurses station monitors in a modular embodiment of the present invention; and FIG. 9 is a block diagram of one embodiment of the nurses station monitor illustrated in FIG. 1.

DESCRIPTION OF PREFERRED EMBODIMENTS

The present invention is concerned with the monitoring of the heart rate of a fetus prior to and during delivery. This heart rate provides an indication of fetal distress associated with a reduction in the amount of oxygen passing to the fetus. This reduced oxygen supply is frequently caused by a constriction in the umbilical cord or cranial pressures which sometimes occurs during labor. For this reason the monitoring of the fetal heart rate can be of importance not only when the mother is in the labor room of a hospital, but also when she is in the delivery room of the hospital.

One embodiment of the present system for monitoring a plurality of fetal heart rates is illustrated in FIG. 1. Each of the fetal heart rates is associated with a particular monitoring channel which is illustrated by reference numerals followed by an associated lower case letter. For example, the lower case letter "*a*" corresponds to a first channel while the reference numerals followed by the letters "*b*" and "*c*" correspond to second and third channels. It will be understood that the concept of the monitoring system can be embodied with any number of the monitoring channels.

Each of the channels a, b, and c includes a transducer assembly 11 (respectively, transducers 11a, 11b and 11c) which senses the associated fetal heart rate to provide a particular, partially detected signal. This signal has particular characteristics associated with the fetal heart rate which are disguised in a high degree of extraneous or artifact noise. The particular signal is introduced by an associated conductor 13 (respectively, conductors 13a, 13b and 13c) to a labor room monitor 15 (respectively, monitors 15a, 15b and 15c).

Each of the labor room monitors 15 detects the heart rate characteristics from the associated signal and generates a pulse train having a rate corresponding to the heart rate. This pulse train modulates a carrier having a frequency which is different for each of the channels a, b, and c. Due to the difference in the carrier frequencies of the channels a, b, and c, the burst signals from the labor room monitors 15a, 15b and 15c can be continuously and simultaneously transmitted on a hand wired data link such as the power lines 17 of the hospital or hospital-like facility.

At a remote location, the modulated carrier signals from the power lines 17 can be introduced to a nurses station master unit 19. The master unit 19 can provide power and a common alarm system for each of a plurality of nurses station monitors 21a, 21b and 21c, each of which monitors one of the fetal heart rates at the nurses station. This modular construction is highly desirable to reduce the expense of the system, to facilitate the addition of new channels to the system, and to reduce the size of the monitoring system at the nurses station.

Due to the highly desirable characteristics of the transducer assemblies 11, which will be discussed in greater detail below, any one of the transducer assemblies 11 can be disconnected from the associated labor room monitor 15 and transported with the mother to the delivery room of the hospital. In the delivery room, the particular signal from the transducer assembly 11 can be introduced on a conductor 23 to an associated delivery room monitor 25.

It is of particular advantage to the present invention that the modulated signals from the labor room monitors 15 can be simultaneously and continuously transmitted on a single conductor pair to the nurses station at a remote location. This conductor pair can be pulled through the walls of the hospital in a manner associated with some of the prior art systems. Of particular advantage however, is the fact that the conductor pair can be the power lines 17 which already exist in the walls of the hospital. These power lines 17 typically include at least four conductors three of which define a different phase with the common fourth conductor. The signals can be transmitted to the nurses station on any one of the phases of the power lines 17. It has been found that the three conductors in the power lines are inductively and capacitively coupled so that the signal introduced onto one of the lines appears in the other two lines typically with only a 20 db attenuation.

FIG. 2 is a detailed illustration of one embodiment of the transducer assembly 11. This particular embodiment includes a sensor assembly 27 coupled to a signal characterizing network 29 by a pair of cables 31 and 33 each including an individually shielded twisted pair.

The signal characterizing network 29 includes a transmitter network 35 and a receiver network 37. The transmitter network 35 provides a high frequency signal which is introduced on the cable 33 to the sensor assembly 27. In the sensor assembly 27, the signal is passed through a transformer 38 and introduced to a transmitting crystal 39. The transmitting crystal 39 is preferably of the type having piezoelectric properties and is characterized by a high side 41 and a low side 43.

In response to the high frequency signal, the piezoelectric crystal 39 deflects at a high frequency to produce ultrasonic waves 45 which are transmitted in a narrow beam to contact the heart 48 of the fetus. When the transmitted waves 45 contact an interface defined by tissues of different densities, reflected waves, shown generally at 49, are produced. If the particular tissue interface, such as the interface between the heart 48 and the adjacent tissues, is moving, the reflected waves 49 have frequency characteristics which are increased or decreased in accordance with the well known Doppler effect. In the reflected waves 49 it is the characteristics produced by the Doppler effect which are of particular interest in the present invention. It will be understood however that these particular characteristics are disguised in a high degree of artifact noise in the reflected waves 49.

The reflected waves 49 are received by at least one receiving crystal 51 preferably having piezoelectric properties and defined by a high side 53 and a low side 55. In response to the reflected waves 49, the crystal 51 deflects to produce a high frequency electrical signal of relatively low power. This signal is introduced through the cable 31 to the receiver network 37 in the signal characterization network 29.

The electrical signal in the cable 31 appears much as that illustrated at 32. The signal 32 is typically defined by a pair of nodes 34 for each heart beat of the fetus. It will be noted that these nodes 34 are disguised in a high degree of artifact noise.

In the preferred embodiment, the crystals 39 and 51 together with the transformer 38 are encased in a housing on a container having a bottom face 56 and a top face 57. The container can be formed from any suitable material such as plastic. A disc 59 made from a clear plastic material such as a material designated as "Lucite" by the DuPont Company is preferably mounted in the plane of the bottom face 56 and the low side 43 of the transmitting crystal 39 is adhered to the disc 59. For each of the receiver crystals 51, a similar Lucite disc 61 can also be provided in the plane of the bottom face 56. The low side 55 of the receiver crystals 51 can be adhered to the associated discs 61.

In operation, the sensor assembly 27 is placed with the bottom face 56 of the container in surface contact with the abdomen of the mother. In this orientation, the discs 59 and 61 provide means for matching the impedance of the crystals 39 and 51 with the tissue of the mother. A suitable acoustical couplant can be applied to the bottom face 56 to further enhance the acoustic coupling of the sensor assembly 27 with the abdomen of the mother. To inhibit motion between the crystals 39 and 51 and the adjacent tissue, the sensor assembly 27 is commonly secured with an elastic adhesive tape.

The transmitter network 35 can include an oscillator 63 such as a Colpitts type oscillator having a frequency of 2 megahertz. The signal from the oscillator 63 can be amplified by a power amplifier 65 prior to its introduction to the cable 33.

The receiver network 37 typically includes a radio frequency amplifier 67 for amplifying the low power signal received from the sensor assembly 27. It is also of particular advantage that the receiver network 37 include a first detector and the highpass filter 69. The highpass filter provides for some low frequency rejection while the first detector at least partially detects the signal received from the sensor assembly 27. The resulting signal from the receiver network 37 is coupled through a separable connector such as that commonly associated with a phone plug 71, for introduction on the conductor 13.

In the signal 32, the particular characteristics associated with the fetal heart beat have a relatively low frequency in a range typically between 50 and 400 Hertz. The artifact noise which is usually associated with the abdominal motion of the mother and the motion of the fetus typically has a frequency less than 100 Hertz. Therefore the highpass filter 69 is preferably tuned to pass only those signals having a frequency greater than 100 Hertz.

The resulting signal from the transducer assembly 11 is of particularly low power, and the particular characteristics of interest in these signals are of low frequency. For these reasons it is desirable to maximize the power of this signal.

One method of doing so is to determine under particular load conditions the series resonant frequency of the crystals 39 and 51 in the sensor assembly 27. The frequency of the oscillator 63 can be tuned to this frequency. The sensor assembly 27 can then be placed in contact with an acoustic coupling device, such as a bag of water, to acoustically couple the transmitter crystal 39 to the receiver crystal 51. Then the radio frequency amplifier 67 and the first detector 69 can be tuned to maximize the power output of the received signal.

It is of particular advantage in the present invention that the signal characterizing electronics in the receiver network 37 and the transmitter network 35 are provided in the transducer assembly 11. This makes it possible for the entire transducer assembly 11 to be unplugged from the labor room monitor 15 and transported with the mother from the labor room to the delivery room of the hospital. This will be particularly appreciated by the mother since the adhesive tape securing the sensor assembly 27 need not be removed from an otherwise sensitive area.

Since the desirable matching characteristics are already provided in the transducer assembly 11, the assembly 11 need not be matched to a particular labor room monitor. The received signal is already maximized in the transducer assembly 11 so that the assembly 11 can be advantageously used with any of the monitors in the labor room or delivery room.

Due to the low power and low frequency of the signal 32 in the assembly 11, it is desirable to shield this signal 32 from low frequency interference of the type commonly associated with high power radio frequency transmissions from AM-FM radio stations and mobile units such as police and radio phone transmissions. To accomplish this purpose, a preferred embodiment of the invention includes a metallic shield 72 which is disposed to at least partially surround the crystals 39 and 51 in the sensor assembly 27. In this embodiment, the transmitter and receiver networks 35 and 37 respectively are encased in a metallic can or shield 73 having a front face 75 and a rear face 77. The cables 31 and 33 are each preferably defined by a twisted pair of conductors enclosed in shields 79 and 81 respectively.

In the cable 31, one of the conductors designated by the numeral 83 is connected to the low side 55 of each of the receiver crystals 51. This particular conductor 83 is preferably coupled to the shield 79 of the cable 31 at the sensor assembly 27. The shield 72 is preferably connected to the shield 81 of the cable 33 at the sensor assembly 27.

In proximity to the can or shield 73, the shields 79 and 81 of the cables 31 and 33 respectively can be connected to the shield 73 at a particular point 85 sometimes referred to as a Mecca ground. In this particular embodiment, it has been found that the interference of extraneous radio signals is minimized if the particular point 85 is disposed in proximity to the rear face 77 of the shield 73.

A block diagram of one embodiment of the labor room monitor 15 is illustrated in FIG. 3. In this embodiment, the signal from the conductor 13 can be initially introduced to a buffer amplifier 87 having a high impedance input and a low impedance output. The primary purpose of the amplifier 87, which may include a unity gain operational amplifier, is to provide signal isolation. The output of the buffer amplifier 87 can be introduced to a bandpass filter 89 which has a preferred passband between 100 and 300 Hertz. From the filter 89 the signal can be introduced through a step attenuator 90, described in greater detail below, to an audio amplifier 91. The amplifier 91 will typically have a gain of 40 db to provide at its output a maximum signal of approximately 4–5 watts for driving a speaker 93.

The sensor assembly 27 is particularly responsive to motion in proximity to the crystals 39 and 51. For this reason it is not surprising that a high magnitude noise signal is produced when the acoustical couplant (not shown) is applied to the face 56 and when the sensor assembly 27 is initially placed in contact with the mother. This high magnitude noise signal can produce a very annoying cracking sound in the speaker 93 if it is not inhibited. In the preferred embodiment, these signals are detected by a threshold detector 95 which is connected to the buffer amplifier 87. The threshold detector 95 can be set to detect signals having magnitudes greater than approximately 70% of the peak to peak magnitude of the cracking noise signals.

When these signals are detected by the detector 95, a resettable monostable multivibrator 97 can be activated to place the step attenuator 90 in an attenuated state. Under normal conditions the step attenuator 90 provides a closed circuit between the filter 89 and the amplifier 91. In response to the signal from the multivibrator 97, the attenuator 90 in a preferred embodiment attenuates the signal from the filter 89 by a magnitude such as 8 or 9 db before it is introduced to the amplifier 91.

To facilitate transmission of the heart rate information on the power line 17, it is desirable that the signal from the buffer amplifier 87 be further processed. The power level of this signal may vary significantly with factors such as the obesity of the mother, placement of the sensor assembly 27, and the motion of the fetus. Power levels in a ratio of 1 to 1,000 are not uncommon.

The signal from the buffer amplifier 87 can be introduced to a network 99 to increase the dynamic range and volume of the signal. The network 99 includes a low branch 100 which amplifies and detects the lower frequencies in the signal. The resulting signal at the output of the low branch 100 can be introduced to a high branch 102 which amplifies and detects the higher frequencies in the signal.

In addition to the different frequency characteristics, the low branch 100 and high branch 102 also have different gain characteristics. Since the signal at the output of the low branch 100 has already been amplified prior to its introduction into the high branch 102, further amplification in the high branch 102 provides the signal with an even higher gain. The signals at the outputs of the low and high channels 100 and 102 can both be introduced to a signal selection circuit 111 described in greater detail below.

In the low branch 100, the signal from the buffer amplifier 87 can be introduced initially to a bridged 'T' filter 101. The filter 101 can be of a conventional type providing further low frequency rejection. The signal from the filter 101 can be introduced to a compression amplifier 103 which compresses the dynamic range of the signal. The gain of the amplifier 103 is preferably nonlinear providing a higher gain at the lower amplitudes. An amplifier and low frequency second detector 105 amplifies and provides for the full wave detection of the signals from the amplifier 103.

In the amplifier and low frequency second detector 105, a signal 32' similar to the signal 32 discussed with reference to FIG. 2, is detected to provide a signal 107. In response to each of a pair of nodes 34' in the signal 32', the detector 104 provides the signal 107 with a single node so that the signal 107 has a frequency of approximately one cycle per heart beat. This signal is introduced on a conductor 109 to the signal selection circuit 111.

The signal on the conductor 109 can also be introduced to a compression amplifier 113 in the high branch 102. The amplifier 113 is similar to the amplifier 103 in the low branch 100 in that it compresses the dynamic range of the signal. However, the compression amplifier 113 preferably has a gain which is higher at the higher frequencies. The resulting signal is introduced through a bandpass amplifier 115 which in the preferred embodiment has a passband between 500 and 1500 Hertz. From the amplifier 115, the signal can be introduced to an automatic gain control (AGC) 116, and a high frequency second detector 117 which provides for the full wave detection of the signal. An AGC control 118 is responsive to the output of the detector 117 to control the AGC 116. The signal from the detector 117 can also be introduced on a conductor 119 to provide a second input to the signal selection circuit 111.

A comparison of the signals on the conductors 109 and 119 is of particular interest to the present invention. The detectors 105 and 117 in the respective branches 100 and 102 each have characteristics for being saturated by a signal of high magnitude. However since the signal at the detector 177 has a higher gain than the signal at the detector 105, the detector 117 will saturate prior to the detector 105.

When the signal at the input to the network 99 has a high power level, the saturation of the detector 117 will limit the amplification of this signal in the high branch 102. Generally speaking, amplification of the high power signals will occur only in the low branch 100 and will be of a relatively low gain. In contrast, a low power signal entering the network 99 will be amplified in both the low branch 100 and the high branch 102. The detector 117 will not saturate so that the additional amplification provided by the branch 102 will provide a relatively high gain for the low power signal.

A preferred embodiment of the signal selection circuit 111 is shown in greater detail in FIG. 4. In this embodiment, the signals on the conductors 109 and 119 are introduced to a summing amplifier 121 which may include an operational amplifier providing linear addition of the input signals. The signal at the output of the summing amplifier 121, hereinafter referred to as the beat signal, will be substantially that shown at 107 in FIG. 3. This signal will have approximately one cycle for each heart beat of the fetus.

This beat signal will include primarily signals within a particular spectrum of frequencies normally associated with fetal heart rates. For example, this frequency spectrum may be defined by the frequencies 1.1 cycles per second and 3.6 cycles per second. This spectrum corresponds to heart rates within a range of 66 to 218 beats per minute.

The particular characteristics of the beat signal which relate to the heart rate will typically be disguised in a high degree of artifact noise. One method for further isolating these particular characteristics is to introduce this signal from the amplifier 121 into a plurality of bandpass amplifiers which are designated by the consecutively odd numerals between 123 and 133 in FIG. 4.

Each of the bandpass amplifiers 123-133 is sharply tuned about a center frequency to pass a portion of the frequencies in the particular frequency spectrum. For example, as shown in FIG. 5, the frequency spectrum between 1.1 and 3.6 cycles per second is divided into six portions each defined by one of the six waveforms shown generally at 135. In this particular embodiment, the waveforms 135 are centered about center frequencies of 1.219, 1.486, 1.811, 2.208, 2.692, and 3.281 cycles per second, which correspond to the heart rates of 73, 89, 109, 132, 162, and 197 beats per minute respectively. These particular center frequencies were chosen so that the waveforms 135 would be geometrically evenly spaced within the spectrum defined by the frequencies of 1.1 to 3.6 cycles per second. The geometric even spacing also insures that the points at which the waveforms 135 intersect have as high a magnitude as possible so that each frequency in the spectrum is passed by at least one of the bandpass amplifiers 123-133.

Each of the bandpass amplifiers 123-133 includes a high Q filter which tends to ring at the fundamental frequency of the associated signal. This is desirable since it provides the signals of the amplifiers 123-133 with an inertia effect much like that of a flywheel. The inertia effect makes the amplifiers 123-133 less responsive to instantaneous changes in the frequency of the rate signal. This tends to sustain the characteristics associated with the fetal heart rate in spite of the high degree of artifact noise present in the signal.

Since the filters in the bandpass amplifiers 123-133 preferably have high Q characteristics, they also have narrow passbands so that more than one of the amplifiers 123-133 will usually be needed to cover the particular spectrum of interest. This particular embodiment has been described with reference to six bandpass amplifiers 123-133 and a particular frequency spectrum between 1.1 and 3.6 Hertz. However, it will be understood that other frequency spectrums may be of interest and the number of amplifiers used to cover a particular spectrum is a matter of design.

The signals from the bandpass amplifiers 123-133 are each introduced to one of a plurality of full wave detectors shown generally at 137. At the output of the detectors 137, each of the signals will include a fundamental frequency associated with a particular heart rate as well as other frequency components such as the harmonics associated with the fundamental frequencies of the signals from the other detectors 137. In one of the signals from the detectors 137, the fundamental frequency will usually have a greater amplitude than in the signals from the other detectors 137. As a general rule, this particular fundamental frequency will correspond to the heart rate of the fetus so that further processing of only the signal from that particular detector 137 is desirable.

One method of selecting this particular signal is to introduce all of the signals at the outputs of the detectors 137 to a voting network 139. This voting network produces a voting signal for each of the amplifiers 123–133 which is introduced on one of a plurality of conductors 141 to a switching network 143. Each of the voting signals on the conductors 141 has a magnitude which is dependent upon the magnitude of the signal from the associated detector 137. Since this magnitude will typically be related to the magnitude of the fundamental frequency in the associated signal, this magnitude is representative of that particular signal which should be reproduced.

It is of importance to note that the magnitude of the signals from the higher frequency amplifiers 129–133 may be increased by the harmonics of the fundamental frequencies in the lower frequency amplifiers 123–127. For this reason, it may be desirable to reduce the magnitude of the voting signal associated with the bandpass amplifier 129 in accordance with the magnitude of the voting signals associated with the amplifiers 123 and 125. Similarly, the voting signal associated with the amplifier 131 can be reduced in accordance with the magnitude of the voting signals associated with the amplifiers 123, 125, and 127. Finally, the voting signal associated with the amplifier 133 can be reduced in accordance with the magnitude of the voting signals associated with the amplifiers 125, 127, and 129. The resulting signals produced by the voting network 139 are introduced on the conductors 141 to the switching network 143 as previously stated.

Each of the signals from the bandpass amplifiers 123–133 are also individually introduced on a plurality of conductors 145 to the switching network 143. The particular voting signal of greatest magnitude on the conductors 141 can be used to enable the associated signal on the conductors 145 through the switching network for introduction on a conductor 147. This particular voting signal on the conductors 141 can also be introduced on a conductor 149 at the output of the signal selection circuit 111 for a purpose discussed in detail below.

Referring again to FIG. 3, it will be noted that the conductor 147 at the output of the signal selection circuit 111 is connected to a threshold trigger 151. The threshold trigger 151 activates a timing network 153 when the magnitude of the signal on the conductor 147 is above some minimum level. Thus the threshold trigger 151 provides a means for determining if a signal actually exists on the conductor 147. When activated by the trigger 151, the timing network 153 provides a stream of pulses in a frequency dependent upon the fundamental frequency in the signal on the conductor 147. Each of these pulses activates a crystal controlled oscillator 155 which has a different carrier frequency for each of the labor room monitors 15. At the output of the oscillator 155, the signal appears as a plurality of pulses modulating a carrier of the associated frequency and having a pulse rate corresponding to the heart rate of the fetus. This signal is introduced to a buffer amplifier 157 which isolates the monitor 15 from the power line 17. Finally this signal is introduced on the power lines 17 along with the pulse modulated signals from the other labor room monitors 15.

It is desirable that the carrier frequencies associated with the oscillators 155 in the different channels a, b, c, be spaced to minimize the spectrum of frequencies transmitted in the power lines 17 while maximizing the isolation of the signals in the different channels. A separation of approximately one kilohertz between the center frequencies of the channels has been found desirable. In a preferred embodiment these carrier frequencies have been adjusted slightly to minimize harmonics distortion in the respective channels. In this preferred embodiment, the oscillator 155 in each of the labor room monitors 15 is tuned to one of the following kilohertz frequencies: 90, 90.8, 91.7, 92.7, 93.8, 105.0, 105.85, 106.60, 107.85, and 109.00.

If the sensor assembly 27 is taken off or falls off, large crashing noises will appear in the signal on the conductor 109. It is desirable that these signals not be transmitted on the power line 17 since they would cause undue concern on the part of personnel at the nurses station.

To inhibit these large crashing noises, the signal on the conductor 109 can be introduced to a crash detector 152. The crash detector 152 determines if the signal is greater than a particular magnitude and if so, it is detected as a crash signal.

The crash signal from the detector 152 is introduced to a threshold amplifier 154 where its magnitude is further compared against the signal on the conductor 149. It will be recalled that the magnitude of the signal on the conductor 149 is indicative of the highest magnitude of the fundamental frequencies present in the signals from the detectors 137. Therefore the signal on the conductor 149 provides an excellent threshold level against which the crash signal can be compared. If the crash signal has a magnitude greater than the signal on the conductor 149, the amplifier 154 can inhibit the timing of the network 153 in which case the crystal controlled oscillator 155 will not be activated by the crash signal.

The signal from the labor room monitors 15 are introduced by the lines 17 to the monitors 21 at the nurses station. These specific monitors 21 will be discussed in greater detail. However, at this point the details of one embodiment of the delivery room monitors 25 will be discussed because many of its features are similar to those discussed with reference to the labor room monitors 15.

Referring now to FIG. 6 it will be noted that the delivery room monitor can be of a construction similar to that of the labor room monitor 15. Thus the conductor 13 can introduce the signal from the transducer assembly 11 to a buffer amplifier 159 such as the buffer amplifier 87. The signal at the output of the amplifier 159 can be introduced to a signal processing network 161 which performs functions similar to those discussed with reference to the network 99 and the boxes 111 and 151–154 in FIG. 3.

The signal from the buffer amplifier 159 is also introduced to an audio channel 163 which performs functions similar to those discussed with reference to the boxes 87, 89, 90, 91, 95, and 97 in FIG. 3. The signal from the audio channel 163 is introduced to a speaker 165. The signal at the output of the signal processing network 161, which is similar to the signal at the output of the timing network 153 in FIG. 3, can be introduced to a monostable multivibrator shown at 167. The multivibrator 167 can be a "one-shot" providing a square wave output signal characterized by one pulse per heart beat. This signal can be introduced through a normally closed switch 169 to an averaging circuit 171 which performs an integration function. The signal at the output of the circuit 171 is introduced through a buffer amplifier 173 to provide isolation and through a normally closed switch 175 to drive a meter 177. The meter 177 is preferably calibrated to provide a direct indication of the fetal heart rate.

In the delivery room, two conditions are of primary concern. If the fetal heart rate falls either above or below a preferred range of heart rates, it may be desirable to provide either one or both of an audible and a visual indication. Since such a signal might indicate insufficient oxygen supply to the fetus, the mother could be shifted to immediately correct this condition.

A second condition of particular interest in the delivery room is that corresponding to an absence of signal at the output of the multivibrator 167. This condition would typically occur when the sensor assembly 27 was not accurately positioned to detect the heart beat. In response to this second condition, a visual indication might be sufficient to indicate a caution state.

To implement these audible and visual indications, a particular embodiment of the monitor 25 includes a high limit set 179 and a low limit set 181. These limits are adjustable to define the preferred range of heart rates for the particular fetus. The high and low limit sets 179 and 181 respectively can be connected to the output of the buffer amplifier 173. If the magnitude of the signal at the output of the amplifier 173 corresponds to a heart rate outside the preferred range, a tone generator 183 can be activated by either one of the sets 179, 181 to introduce an audio signal through a normally closed alarm switch 187 to the speaker 165. In a preferred embodiment, the signal from the generator 183 may have a frequency of 3 kilohertz.

Under some circumstances it may be desirable to provide means for inhibiting the audible alarm. When this inhibiting means is activated, it may additionally be desirable to provide a visual indication so that one is cautioned not to rely solely upon the audible signal. This visual indication can take the form of a light 185 burning with a constant brilliance. It may also be desirable to provide a second visual indication if the indicated heart rate falls to a value of substantially zero. This second indication can be implemented by providing the light 185 with blinking characteristics.

The audio signal inhibiting function as well as the first and second visual indications can be implemented by a three pole, double throw switch 187. The switch 187 includes common terminals 189, 191, and 193 which can be alternately switched between the terminals 195, 197, 199 respectively and the terminals 201, 203, and 205 respectively. The filament of the light 185 can be connected at one end to a positive potential +E, and at the other end through a conductor 186 to the terminals 193 and 197 of the switch 187.

A caution oscillator 207 produces a signal defined by pulses occurring periodically at intervals such as 2½ seconds. The output of the caution oscillator 207 is introduced on a conductor 209 to a first inverting amplifier 211. The amplifier 211 provides on a terminal 213 a signal having characteristics inverted from the characteristics of the signal on the conductor 209. The terminal 213 can be connected to the terminal 191 in the switch 187.

A second inverting amplifier 215 can be connected to receive the signal on the terminal 213. The amplifier 215 provides at its output a signal having characteristics inverted from the characteristics of the signal on the terminal 213. The output of the amplifier 215 can be connected to the terminal 205 of the switch 187.

Under normal conditions, the conductor 209 is connected through a normally closed electronic switch 219 to a reference potential such as ground. This provides on the conductor 209 a constant negative potential which in turn produces a constant positive potential on the terminal 213 and a constant negative potential on the terminal 205. The effect of these normal conditions is discussed in greater detail below.

The output of the tone generator 183 can be connected to the common terminal 189 and the speaker 165 can be connected to the terminal 195. With the switch 187 in a first operating position, as illustrated in FIG. 6, the terminal 189 is connected to the terminal 195 so that the audio signal is introduced to the speaker 165.

In this first operating position, the constant positive potential which normally appears on the terminal 191 is introduced through the terminal 197 to the conductor 186. Since both sides of the light 185 receive constant positive potentials, there is no potential difference to illuminate the light 185 under these normal circumstances.

If it is desirable to inhibit the audio signal, the switch 187 can be thrown to the second operating position so that the common terminals 189-193 break with the terminals 195-199 respectively and make with the terminals 201-205 respectively. In addition to breaking the connection between the tone generator 183 and the speaker 185, movement of the switch to the second operating position connects the terminal 193 with the terminal 205. The constant negative potential which normally appears on the terminal 205 is therefore introduced to the conductor 186. This will provide a difference in potential across the light 185 which will illuminate the light 185 at a constant brilliance. Thus the light 185 glowing with a constant brilliance provides an indication that one should not rely solely upon the audio signal from the speaker, but rather should rely upon the meter 177 for an indication of fetal distress.

The signal at the output of the monostable multivibrator 167, which provides a pulse for each heart beat, can be used to repeatedly reset a monostable multivibrator 217 with each pulse. When the heart rate falls below a particular level, such as substantially zero, the pulses from the multivibrator 167 are sufficiently spaced so that the multivibrator 217 is not reset within a particular interval of time. Under these conditions, a signal from the multivibrator 217 opens the normally closed switches 169, 175, and 219. With the switch 219 in an open state, the negative going pulses from the caution oscillator 207 are introduced to the amplifier 211. This provides positive going pulses on the terminal 213 and negative going pulses on the terminal 205. If the speaker inhibiting switch 187 is in the first operating position, the pulses on the terminal 191 will cause the light 185 to blink. If the switch 187 is in the second operating position, the pulses on the terminal 205 will cause the light 185 to blink. Thus whether the switch 187 is in the first or second operating position, the light 185 will be intermittently illuminated. With these blinking characteristics, the light 185 will indicate that the fetal heart rate has fallen to substantially zero. This will normally mean that the sensor assembly 27 has become dislodged so that appropriate measures can be taken to reconnect the assembly 27.

The averaging circuit 171 is typically an integrator which integrates the pulses from the multivibrator 167 over a period of time. If the sensor assembly 27 becomes dislodged, no pulses will be emitted from the multivibrator 167 and the average of the circuit 171, unless otherwise sustained, will discharge to zero. This is undesirable since the circuit 171 will have to build up over the relatively long integration period before the meter 177 will again provide an accurate indication of heart rate.

The present invention provides for the storage of information related to the preceding heart rate when the present heart rate has a value of substantially zero. As noted, when the heart rate goes to zero, the switches 169 and 175 are opened. This inhibits the discharge path of the averaging circuit 171 so that the signal corresponding to the preceding heart rate is stored in the circuit 171. The opening of the switch 175 dumps the signal from the amplifier 173 so that the meter 177 is permitted to go to a zero value.

When the sensor assembly is reconnected and the pulses from the multivibrator 167 reoccur, the switches 169 and 175 will be closed and the previous average stored in the circuit 171 will jump the meter 177 to approximately the previous indication. Further integration proceeds from this point so that there is no delay associated with the integration of the averaging circuit 171.

Before proceeding with a detailed discussion of the master unit 19 and the monitors 21 at the nurses station, it will be noted that many of the components associated with these units are similar to those discussed with reference to FIG. 6. Where the function of these components is substantially the same, they will be numbered with the same reference numerals followed by a prime indication.

As previously discussed with reference to FIG. 1, the signals from the labor room monitors 15 are introduced onto the power line 17 for transmission to the nurses station at a remote location. The heart rate of each of the monitors 15 is modulated on a different carrier frequency for transmission on a single phase of the power line 17. The nurses station master unit 19 receives this composite signal from the power line 17 and introduces the signal through a data link buffer 221 which blocks the 60 cycle power and permits the modulated carriers of the heart rate signals to pass. These modulated carriers are introduced on a bus designated in FIG. 7 by the reference numeral 223. A power supply 225 is also connected to the power lines 17 and provides an unregulated power signal such as 22 volts dc. This signal is introduced on a bus 227. Ground return for the heart rate signals and power signals on the buses 223 and 227 respectively is provided on a bus 226.

One of the significant features of the present invention is the modular concept of the monitors 21 at the nurses station. Many of the functions which are common to the monitors 21 can be singularly implemented in the master unit 19 rather than duplicated in each of the monitors 21. On a bus 229, any alarm signal from one of the monitors 21 can be introduced to an alarm tone generator 231 and through an alarm level control 233 to activate a speaker 165'. The control 233 can be a potentiometer providing means for adjusting the level of the audible signal.

One embodiment of the modular concept of the present invention is shown in FIG. 8. As illustrated, the nurses station monitors 21 can be coupled to form a series of modules each having a connection for contacting the buses 223, 227, and 229 in the modules preceding in the series and each providing a connection on the buses 223, 227, and 229 for modules following in the series.

Referring now to FIG. 9, it will be noted that the nurses station monitors 21 can be constructed to tap the signals from the bus 223 and to introduce these signals into a crystal filter 235. The filter 235 is tuned to the carrier frequency of the crystal controlled oscillator 155 in the associated labor room monitor 15. Thus the filter 235 insures that only the signal associated with the particular heart rate of the associated fetus is processed by the associated nurses station monitor 21. The signal is introduced through an automatic gain control 237 and an amplifier 239 having a gain such as 60 db.

The amplified signal can be detected in a first detector 241 and introduced through a threshold and squaring amplifier 243 to a monostable multivibrator 167'. The threshold of the squaring amplifier 243 is preferably set above the level of the highest interfering noise. The output of the first detector 241 can be applied to a second detector 242 and the detected signal introduced through a low pass filter 244 to control the gain level of the automatic gain control 237.

In the manner previously discussed with reference to the delivery room monitor 25, the signal from the multivibrator 167' can be passed through normally closed electrical switches 169' and 175', averaged in a circuit 171', buffered in an amplifier 173', and displayed on a meter 177'.

Also as previously discussed, the preferred range of heart rates can be set by high and low limit sets 179' and 181', respectively. In response to heart rates beyond these high and low limits, the sets 179' and 181' initiate signals which are introduced to a pair of respective delay networks 180 and 182. Following the delay associated with the network 180 or 182, one of a pair of associated latches 245 and 247 will be toggled. With either of the latches 245 or 247 in a toggled stage, a voltage level will be applied through a normally closed switch 251 to the bus 229. This voltage level energizes the audio alarm in the master unit 19 at the nurses station. The delay associated with the networks 180, 182 is preferably in the order of 15 seconds. A delay of this duration inhibits limit signals of short duration from toggling the latches 245 and 247. This reduces the number of unwanted alarms.

It is not uncommon for a nurse to be absent from the nurses station at a time when the heart rate of one of the fetuses extends beyond the associated preferred range of heart rates. Under these circumstances the audible signal is desirable to hasten the return of the nurse to the station to determine which of the fetuses is in distress. In some cases the heart rate of the fetus may have returned to the preferred range of heart rates so that a mere meter indication would not tell the nurse whether the distress was associated with a high or a low heart rate.

In a preferred embodiment, the latches 245 and 247 perform much as flip-flops thereby sustaining the particular limit or distress signal. A high level indicator 261 is connected to the output of the latch 245 to provide a visual indication of high heart rate distress. Similarly a low level indicator 259 is connected to monitor the output of the latch 247. The latches 245 and 247 provide a means for sustaining the visual indications provided by the indicators 259 and 261 as well as the audible indication provided by the speaker 165 in the master unit 19. Therefore, even if the fetal heart rate returns to the preferred range, the audible alarm will continue and the nurse will be provided with an indication as to whether the distress was associated with a high or a low heart rate.

It may be desirable to be able to turn off the audio alarm once it has been noted which channel is in the alarm state. This is particularly true when multiple channels are in use since the audio alarm is common to all channels. In the illustrated embodiment of the invention, the alarm signals provided by the latches 245 and 247 are introduced through an alarm-off enable circuit 249 to energize an alarm-off switch 253. When the switch 253 is energized and activated, a latch 263 which is connected to the latches 245 and 247 is toggled. In this toggled state, the latch 263 opens the normally closed switch 251 to inhibit introduction of the alarm signal on the bus 229. When the latch 263 is toggled, an alarm-off signal is introduced through a terminal 213' to illuminate a caution light 185'. This illumination can be of a constant brilliance to indicate that the audio alarm has been deactivated.

It may also be of advantage to insure that the audio alarm cannot be disabled prior to an alarm condition. For this reason, the alarm-off enable circuit 249 is provided between the latches 245, 247 and the switch 253. This circuit 249 energizes the switch 253 only in response to alarm signals produced by the latches 245 and 247. Thus the closing of the alarm-off switch 253 under other than alarm conditions will not toggle the latch 263.

The preferred embodiment includes the means for clearing the audio alarm-off condition once the output of the buffer amplifier 173' returns to the desired limits defined by the sets 179' and 181'. A reset enable circuit 255 is connected to the outputs of the sets 179' and 181'. With both of these outputs valid, the reset enable circuit 255 can energize a reset switch shown generally at 257. Once the reset switch 257 has been enabled and momentarily closed, the three latches 245, 247 and 263 are restored to their normal operating conditions.

In the preferred embodiment, the nurses station monitor 21 has a caution state which is energized when there is a loss of signal at the monitor 21. As previously discussed, this typically nondistress condition can be caused inadvertantly when the transducer assembly 11 is dislocated or deliberately when the mother is moved to the delivery room. In any event, these conditions can be brought to the attention of the nursing staff with a visual display, such as a blinking light. It will be noted that in this embodiment, there is no audio alarm during this caution state; the audio alarm is reserved for true fetal distress.

A visual alarm can be provided in this caution state with much of the circuitry previously discussed. A resettable monostable multivibrator 217' can be connected between the output of the multivibrator 167' and the normally closed switch 169'. In response to a data dropout of about 10 seconds, the multivibrator 217' will open the switch 169' and the latest heart rate information will be stored in the averaging circuit 171'. The output of the multivibrator 217' can be introduced through a delay 218 to the normally closed electrical switch 175'. After the delay provided by the delay 218, the switch 175' is opened and the display of the meter 177' goes abruptly to zero.

A caution oscillator 207' provides a signal which is introduced to a normally open switch 219'. This switch 219' is closed when the delay 218 times out and the oscillating signal is introduced through a buffer amplifier 211' to intermittently energize the caution lamp 185'.

As noted in the previous discussion, many of the features of the present invention provide significant advantages not present in the fetal heart rate monitors of the prior art. One such feature is that associated with the particular shielding concept discussed with reference to the transducer assembly 11 of FIG. 2. The provision of the shields 72, 73, 79, and 81 together with their common connection to the point 85 provides optimum shielding to inhibit the interference of spurious signals which are mixed with the ultrasonic carrier signal.

The provision of the signal characterizing network 29 in the transducer assembly 11 is also of particular advantage. The assembly 11 can be transported with the mother between the labor room and the delivery room and can be connected with any of the monitors at those locations. With the provision of the signal characterizing network in the assembly 11, the signal at the output of the assembly 11 is optimized before it is connected to any of the monitors 15 or 25.

The heart rate signals are modulated on different carrier frequencies so that they can be transmitted through a single phase of the house wiring. No hard wire need be drawn within the walls of the hospital to provide signals at a remote location such as the nurses station.

At the nurses station, the monitors can be constructed in a modular arrangement consisting of a power unit and a plurality of modules connected in a series to the power unit. Similar functions such as the alarm function can be singularly implemented in the power unit. The modular construction therefore significantly reduces the size of the apparatus used to monitor several heart rates. The modules at the nurses station can be provided with the indicators 259 and 261 so that the nurse responding to an alarm condition can ascertain if the heart rate was high or low without reference to the meter 177'.

If the sensor assembly 27 becomes dislocated from the mother, the present invention provides means for storing information related to the preceding heart rate so that with the reconnection of the sensor assembly 27 there is no delay associated with the buildup of an integration circuit.

In a specific embodiment of the invention, separate alarm indications can be provided to distinguish a decelerating heart rate from a heart rate having a step function which instantaneously falls to zero. Since the decelerating heart rate is typically associated with fetal distress, the associated alarm indication can be made audible. A heart rate having a step function is typically associated with a nondistress condition such as a dislocated sensor 27. In this caution state, the alarm may merely provide a visual indication.

The signal selection circuit 111 in the labor room monitor 15 is of particular advantage since it provides means for providing a high degree of selectivity in protecting the heart rate from a high degree of artifact noise present in the ultrasonic signal. This selection circuit 111 makes it possible to rely entirely upon the ultrasonic transducer assembly 11 in sensing the heart rate of the fetus.

Although these concepts have been discussed with reference to particular embodiments, it will be appreciated by those skilled in the art that the concepts can be otherwise embodied to perform the functions and provide the significant advantages associated with the present invention. For this reason the scope of the invention should be ascertained only with reference to the following claims.

We claim:

1. A system for use with a prospective mother to monitor the heart rate of a fetus within the prospective mother, comprising:

a sensor assembly disposed in contact with the prospective mother and in proximity to the heart of the fetus, the sensor assembly being responsive to the heart beat of the fetus to provide a first electrical signal having particular characteristics dependent upon the heart rate of the fetus;

a monitor respective to the first electrical signal to provide signals representing the heart rate of the fetus;

first means included in the monitor and variable to define a preferred range of heart rates for the fetus;

second means included in the monitor and responsive to the signals from the monitor to provide a first indication when the particular characteristics of such signals indicate a heart rate outside of the preferred range of heart rates;

third means included in the monitor and responsive to the signals from the monitor to provide a second indication when the particular characteristics of such signals indicate a heart rate of substantially zero;

the first indication signaling a distressed fetus and the second indication signaling loss of contact between the sensor assembly and the mother and the fetus;

fourth means operatively coupled in the monitor means to the second means to provide an audible indication when the heart rate of the fetus is outside of the preferred range;

fifth means operatively coupled in the monitor means to the second means to provide a visual indication when the heart rate of the fetus is outside of the preferred range;

sixth means operatively coupled in the monitor means to the fourth and fifth means to activate a particular one of the fourth and fifth means;

the sensor means being located such that the particular characteristics of the first signal indicate a particular heart rate and, when the sensor means is dislocated, the particular characteristics of the first signal indicate a heart rate of substantially zero;

seventh means responsive to the production by the monitor of signals indicating a heart rate of substantially zero to store for at least a particular period of time a quantity indicative of the last heart rate of the fetus before the production of the signals indicating a heart rate of substantially zero; and eighth means responsive to the signals stored by the seventh means to jump the first indication of the monitor to the heart rate stored by the seventh means after the resumption in the monitor of signals indicating a heart rate of the fetus other than zero, whereby a rapid indication of the heart rate is provided as soon as the sensor means is relocated.

2. A system for monitoring the heart rate of each of a plurality of fetuses in each of a plurality of expectant mothers, including:

a first plurality of transducers each constructed to be disposed in external proximity to the abdomen of a different one of the expectant mothers to send first signals to a particular frequency to the fetus in that monitor;

a second plurality of non-directional transducers each constructed to be disposed in external proximity to the abdomen of a different one of the expectant mothers and each responsive to the heart beat of the fetus in that mother to produce a second signal having frequency characteristics dependent upon the frequency of the signals from the heart rate of the associated one of the transducers and upon the associated fetus;

a plurality of means each operatively coupled to an individual one of the transducers in the second plurality of demodulating the signals from the operatively coupled transducer to produce signals representing the heart beat of the fetus and representing noise;

a plurality of means each coupled to an individual one of the last mentioned means for processing the signals from the individual one of the last mentioned means to recover the signals representing the heart beat of the fetus and to deemphasize the signals representing noise;

a plurality of transmitting means for generating a plurality of carrier signals each having an individual carrier frequency, each of the transmitting means being responsive to the processed signals representing the heart beat of the fetus from the individual one of the transducers in the second plurality to modulate the carrier signals from such transmitting means with the processed signals from the individual one of the transducers in the second plurality to provide one of a plurality of modulated carrier signals each having the individual frequency;

at least a pair of electrical conductors extending from the plurality of transmitting means to a remote location and responsive to the modulated carrier signals from the plurality of transmitting means to introduce simultaneously the modulated carrier signals to the remote location;

a plurality of frequency responsive means disposed at the remote location, each of the frequency responsive means being responsive to an individual one of the different carrier frequencies in the pair of electrical conductors to receive the modulated carrier signals from only an individual one of the transmitting means;

a plurality of demodulating means each associated with an individual one of the frequency responsive means for demodulating the modulated carrier signals to provide an indication of the heart rates of an individual one of the fetuses, a master unit for providing electrical power for the plurality of frequency responsive means and the plurality of demodulating means;

a plurality of modular units constructed to be connected to the master unit in series and each of the modular units including a first bus for receiving the modulated carrier signals from the modular units preceding in the series and for introducing the modulated carrier signals to the modular units following in the series, each of the processing means including a plurality of band pass amplifiers each operative in an individual band of frequencies within the range of frequencies in which the heart rate of the fetus occurs and the processing means further including a plurality of detector means each associated with an individual one of the band pass amplifiers and the processing means further including voting means responsive to the signals from the plurality of detector means for selecting the signals from an individual one of the detector means in accordance with the relative amplitudes of such signals and the processing means including means responsive to the signals selected by the voting means for passing only such signals to the transmitting means;

means variable to define a preferred range of heart rates for the associated fetus;

threshold detection means responsive to the associated modulated carrier signals to provide an alarm signal when the heart rate of the associated fetus in not within the preferred range of heart rates;

a bus disposed in each of the demodulating means and connected to introduce the alarm signal from the demodulating means following in the series to the demodulating means preceding in the series; and alarm means responsive to the alarm signal on the bus to provide an audible indication when the heart rate of any one of the fetuses is beyond the preferred range of heart rates for the associated fetus.

3. A system for monitoring the heart rate of each of a plurality of fetuses in each of a plurality of expectant mothers, including:

a first plurality of transducers each constructed to be disposed in external proximity to the abdomen of a different one of the expectant mothers to send first signals to a particular frequency to the fetus in that monitor;

a second plurality of non-directional transducers each constructed to be disposed in external proximity to the abdomen of a different one of the expectant mothers and each responsive to the heart beat of the fetus in that mother to produce a second signal having frequency characteristics dependent upon the frequency of the signals from the heart rate of the associated one of the transducers and upon the associated fetus;

a plurality of means each operatively coupled to an individual one of the transducers in the second plurality of demodulating the signals from the operatively coupled transducer to produce signals representing the heart beat of the fetus and representing noise;

a plurality of means each coupled to an individual one of the last mentioned means for processing the signals from the individual one of the last mentioned means to recover the signals representing the heart beat of the fetus and to deemphasize the signals representing noise;

a plurality of transmitting means for generating a plurality of carrier signals each having an individual carrier frequency, each of the transmitting means being responsive to the processed signals representing the heart beat of the fetus from the individual one of the transducers in the second plurality to modulate the carrier signals from such transmitting means with the processed signals from the individual one of the transducers in the second plurality to provide one of a plurality of modulated carrier signals each having the individual frequency;

at least a pair of electrical conductors extending from the plurality of transmitting means to a remote location and responsive to the modulated carrier signals from the plurality of transmitting means to introduce simultaneously the modulated carrier signals to the remote location;

a plurality of frequency responsive means disposed at the remote location, each of the frequency responsive means being responsive to an individual one of the different carrier frequencies in the pair of electrical conductors to receive the modulated carrier signals from only an individual one of the transmitting means;

a plurality of demodulating means each associated with an individual one of the frequency responsive means for demodulating the modulated carrier signals to provide an indication of the heart rates of an individual one of the fetuses;

a master unit for providing electrical power for the plurality of frequency responsive means and the plurality of demodulating means;

a plurality of modular units constructed to be connected to the master unit in series and each of the modular units including a first bus for receiving the modulated carrier signals from the modular units preceding in the series and for introducing the modulated carrier signals to the modular units following in the series, each of the processing means including a plurality of band pass amplifiers each operative in an individual band of frequencies within the range of frequencies in which the heart rate of the fetus occurs and the processing means further including a plurality of detector means each associated with an individual one of the band pass amplifiers and the processing means further including voting means responsive to the signals from the plurality of detector means for selecting the signals from an individual one of the detector means in accordance with the relative amplitudes of such signals and the processing means including means responsive to the signals selected by the voting means for passing only such signals to the transmitting means, the threshold detector means being constructed to provide the alarm signal with first characteristics when the heart rate of the associated fetus is higher than the preferred range of heart rates and with second characteristics when the heart rate of the associated fetus is lower than the preferred range of heart rates and wherein the system further comprises:

a first indicator included in each of the demodulating means and responsive to the first characteristics of the alarm signal to provide a first visual indication;

a second indicator included in each of the demodulating means and responsive to the second characteristics of the alarm signal to provide a second visual indication;

means included in each of the demodulating means for sustaining the indication of the first and second indicators even after the heart rate of the associated fetus returns to the preferred range of heart rates; and resettable means operable after the heart rate of the associated fetus has returned to the preferred range of heart rates for inhibiting the alarm signal and the first and second visual indications.

4. Apparatus for monitoring the heart rate of a fetus in an expectant mother, comprising:

a housing;

a first ultrasonic transducer included in the housing and constructed to be disposed externally of the abdomen of the expectant mother to transmit signals at a particular frequency to the fetus;

a second ultrasonic transducer included in the housing and constructed to be disposed externally on the abdomen of the expectant mother to receive from the fetus the signals at the particular frequency but modulated by the heart rate of the fetus;

an ultrasonic transducer assembly, including the first and second transducers, constructed to provide for the transmission of the signals at the particular frequency to the fetus and to receive the modulated signals from the fetus;

the transducer assembly including means included in the housing for matching the impedance of the first transducer to the impedance of the abdomen of the expectant mother and means for matching the impedance of the second transducer to the impedance of the abdomen of the expectant mother;

monitor means responsive to the modulated characteristics of the received signal to detect such modulations for the production of indications representing the heart rate of the fetus, the monitor means including means for passing the modulations and rejecting artifact noise;

coupling means releasably connecting the transducer assembly with the monitor means to introduce the modulated signals to the monitor means;

means for providing a carrier signal having a particular frequency;

means for modulating the carrier signals with the signals passing through the monitor means and for transmitting the signals to a distant position;

means at the distant position for demodulating the signals transmitted to the distant position;

the transducer assembly including the first and second transducers being constructed to be disposed in proximity to the heart of the fetus externally on the abdomen of the expectant mother, the first transducer being constructed to produce signals of the particular frequency and the second transducer being responsive to the heart beat of the fetus to provide the particular signal with frequency modulations dependent upon the heart rate of the fetus;

signal characterization network means fixedly connected to the transducer assembly and operatively coupled to the first transducer to obtain the production of the signals of the particular frequency and operatively coupled to the second transducer and responsive to the signal received by the second transducer of the transducer assembly to partially detect the signal modulating the particular frequency, the signal characterization network means having characteristics responsive to the resonant frequency of the transducer assembly to maximize the power of the modulated signal and to introduce the modulated signal to the monitor means, the rejecting means in the monitor means including means responsive to abrupt signals of large magnitude resulting from changes in the disposition of the transducer assembly unrelated to the heart rate of the fetus for inhibiting such signals from affecting the indications of fetal heart rate and means responsive in the monitor means to the disposition of the transducer assembly out of proximity with the heart of the fetus for retaining for at least a particular period of time the last indication provided by the monitor means of the fetal heart rate, the transducer assembly further comprising:

a first cable including a first conductor for introducing the signal of the particular frequency to the first transducer;

a second cable including a second conductor for introducing the modulated signal to the signal characterization network means from the second transducer;

a first metallic shield surrounding the first conductor in the first cable;

a second metallic shield surrounding the second conductor in the second cable;

a third metallic shield at least partially surrounding the first and second transducers in the transducer assembly;

a fourth metallic shield at least partially surrounding the signal characterization network and coupled at one end to the monitor means and coupled at the other end to the first and second cables; and means electrically connecting the first, second, third and fourth metallic shields to provide a reference potential for the first, second, third and fourth metallic shields.

5. The combination set forth in claim 4 wherein the monitor means includes a plurality of band pass amplifiers each constructed to pass signals having frequencies in an individual range and wherein the modulations in the received signal are introduced to the band pass amplifiers to obtain the passage of signals through the amplifiers in accordance with the frequency characteristics of the modulations and the frequency characteristics of the amplifiers and wherein the rejecting means in the monitor means includes means for weighing the amplitudes of the signals passing through each of the band pass amplifiers in accordance with the frequency characteristics of each of the amplifiers.

6. A system for monitoring the heart rate of a fetus in an expectant mother, comprising:

a housing;

a first transducer included in the housing and constructed to be disposed on the abdomen of the expectant mother to transmit signals at a particular frequency to the fetus;

a second transducer included in the housing and constructed to be disposed on the abdomen of the expectant mother to receive from the fetus the signals at the particular frequency modulated by the heart rate of the fetus;

first means included in the housing for matching the impedance of the first transducer to the impedance of the abdomen of the expectant mother;

second means included in the housing for matching the impedance of the second transducer to the impedance of the abdomen of the expectant mother;

transducer assembly means including the first and second transducers from the first and second means for providing for the transmission of the signals at the particular frequency and the reception of the modulated signals and a high degree of artifact noise;

a plurality of filter means collectively responsive to the particular spectrum of frequencies in the modulated signals and individually tuned sharply to pass a filtered signal including frequencies within a relatively narrow and individual portion of the particular frequency spectrum, each of the filter means being constructed to pass filtered signals including fundamental frequencies and harmonic frequencies within its relatively narrow and individual portion of the frequency spectrum;

third means responsive to the filtered signals passing through the plurality of filter means for enabling the particular one of the filter means passing the filtered signal having the greatest magnitude;

fourth means responsive to the fundamental frequency of the signal passed by the enabled one of the filter means for demodulating such signal to provide an indication of the heart rate of the fetus;

a voting network including a plurality of voting means each associated with an individual one of the filter means for providing a voting signal having a magnitude dependent upon the magnitude of the associated filtered signal; and a channel selection network responsive to the voting signals from the plurality of voting means for enabling the filtered signal associated with the voting signal of greatest magnitude, the individual voting means including:

fifth means for increasing the magnitude of the voting signal in the voting means relative to the magnitude of the harmonics in the voting means in accordance with the magnitude of the fundamental frequency of the signal introduced to the voting means whereby each of the voting signals has a magnitude primarily dependent upon the magnitude of the fundamental frequency.

7. The system set forth in claim 6 including sixth means responsive to the production by the signal means of a signal outside of the particular spectrum of frequencies for producing an audible signal representing the production of such a signal and seventh means responsive to the production by the signal means of a signal outside of the particular spectrum of frequencies for providing a visual indication representing the production of such a signal and eighth means operatively coupled to the sixth and seventh means for activating the sixth means at first particular times and the seventh means at second particular times and ninth means responsive to a change in the disposition of the transducer means to a position removed from the heart of the fetus for providing a visual indication even upon the activation of the sixth means by the eighth means.

8. Apparatus for monitoring the heart rate of a fetus in an expectant mother, comprising:

a housing;

a first ultrasonic transducer included in the housing and constructed to be disposed externally of the abdomen of the expectant mother to transmit signals at a particular frequency to the fetus;

a second ultrasonic transducer included in the housing and constructed to be disposed externally on the abdomen of the expectant mother to receive from the fetus the signals at the particular frequency but modulated by the heart rate of the fetus;

an ultrasonic transducer assembly, including the first and second transducers, constructed to provide for the transmission of the signals at the particular frequency to the fetus and to receive the modulated signals from the fetus;

the transducer assembly including means included in the housing for matching the impedance of the first transducer to the impedance of the abdomen of the expectant mother and means for matching the impedance of the second transducer to the impedance of the abdomen of the expectant mother;

monitor means responsive to the modulated characteristics of the received signal to detect such modulations for the production of indications representing the heart rate of the fetus, the monitor means including means for passing the modulations and rejecting artifact noise;

coupling means releasably connecting the transducer assembly with the monitor means to introduce the modulated signals to the monitor means;

means for providing a carrier signal having a particular frequency;

means for modulating the carrier signals with the signals passing through the monitor means and for transmitting the signals to a distant position;

means at the distant position for demodulating the signals transmitted to the distant position;

means responsive to a change in the disposition of the transducer assembly means to a position removed from the heart of the fetus for providing for at least a particular period of time a signal having a frequency representing the last rate of the heart beat of the fetus before such change in disposition; and means responsive to a restoration of the transducer assembly means on the abdomen of the expectant mother for restoring the signal having the last rate of the heart beat;

the monitor including a plurality of filter means collectively responsive to all of the heart rates within the preferred range and individually responsive to a narrow spectrum of frequencies within the preferred range and the monitor further including voting means responsive to the signals from the filter means in the plurality for enabling only the filter means passing the signal of the greatest magnitude.

9. The system set forth in claim 8 wherein each of the filter means is operative to attenuate harmonics within its narrow spectrum in relation to fundamental frequencies within its narrow spectrum to cause the voting means to be responsive essentially only to the fundamental frequencies in the preferred range.

10. The system set forth in claim 9 wherein means are included in the monitor for inhibiting any effect on the signals from the monitor of changes in the disposition of the sensor assembly relative to the prospective mother.

11. Apparatus for monitoring the heart rate of a fetus in an expectant mother, comprising:

a housing;

a first ultrasonic transducer included in the housing and constructed to be disposed externally of the abdomen of the expectant mother to transmit signals at a particular frequency to the fetus;

a second ultrasonic transducer included in the housing and constructed to be disposed externally on the abdomen of the expectant mother to receive from the fetus the signals at the particular frequency but modulated by the heart rate of the fetus;

an ultrasonic transducer assembly, including the first and second transducers, constructed to provide for the transmission of the signals at the particular frequency to the fetus and to receive the modulated signals from the fetus;

the transducer assembly including means included in the housing for matching the impedance of the first transducer to the impedance of the abdomen of the expectant mother and means for matching the impedance of the second transducer to the impedance of the abdomen of the expectant mother;

monitor means responsive to the modulated characteristics of the received signal to detect such modulations for the production of indications representing the heart rate of the fetus, the monitor means including means for passing the modulations and rejecting artifact noise;

coupling means releasably connecting the transducer assembly with the monitor means to introduce the modulated signals to the monitor means;

means for providing a carrier signal having a particular frequency;

means for modulating the carrier signals with the signals passing through the monitor means and for transmitting the signals to a distant position;

means at the distant position for demodulating the signals transmitted to the distant position;

the transducer assembly including the first and second transducers being constructed to be disposed in proximity to the heart of the fetus externally on the abdomen of the expectant mother, the first transducer being constructed to produce signals of the particular frequency and the second transducer being responsive to the heart beat of the fetus to provide the particular signal with frequency modulations dependent upon the heat rate of the fetus, signal characterization network means fixedly connected to the transducer assembly and operatively coupled to the first transducer to obtain the production of the signals of the particular frequency and operatively coupled to the second transducer and responsive to the signal received by the second transducer of the transducer assembly to partially detect the signal modulating the particular frequency, the signal characterization network means having characteristics responsive to the resonant frequency of the transducer assembly to maximize the power of the modulated signal and to introduce the modulated signal to the monitor means, means responsive in the monitor means to the disposition of the transducer assembly out of proximity to the heart rate of the fetus for retaining for at least a particular period of time the last indications provided by the monitor means of the fetal heart rate; and means for restoring the last indications provided by the monitor means of the fetal heart rate when the transducer assembly is returned in proximity to the heart rate of the fetus.

12. Apparatus for monitoring the heart rate of a fetus in an expectant mother, comprising:

a housing;

a first ultrasonic transducer included in the housing and constructed to be disposed externally of the abdomen of the expectant mother to transmit signals at a particular frequency to the fetus;

a second ultrasonic transducer included in the housing and constructed to be disposed externally on the abdomen of the expectant mother to receive from the fetus the signals at the particular frequency but modulated by the heart rate of the fetus;

an ultrasonic transducer assembly, including the first and second transducers, constructed to provide for the transmission of the signals at the particular frequency to the fetus and to receive the modulated signals from the fetus;

the transducer assembly including means included in the housing for matching the impedance of the first transducer to the impedance of the abdomen of the expectant mother and means for matching the impedance of the second transducer to the impedance of the abdomen of the expectant mother;

monitor means responsive to the modulated characteristics of the received signal to detect such modulations for the production of indications representing the heart rate of the fetus, the monitor means including means for passing the modulations and rejecting artifact noise;

coupling means releasably connecting the transducer assembly with the monitor means to introduce the modulated signals to the monitor means;

means for providing a carrier signal having a particular frequency;

means for modulating the carrier signals with the signals passing through the monitor means and for transmitting the signals to a distant position;

means at the distant position for demodulating the signals transmitted to the distant position;

the transducer assembly including the first and second transducers being constructed to be disposed in proximity to the heart of the fetus externally on the abdomen of the expectant mother, the first transducer being constructed to produce signals of the particular frequency and the second transducer being responsive to the heart beat of the fetus to provide the particular signal with frequency modulations dependent upon the heart rate of the fetus;

signal characterization network means fixedly connected to the transducer assembly and operatively coupled to the first transducer to obtain the production of the signals of the particular frequency and operatively coupled to the second transducer and responsive to the signal received by the second transducer of the transducer assembly to partially detect the signal modulating the particular frequency, the signal characterization network means having characteristics responsive to the resonant frequency of the transducer assembly to maximize the power of the modulated signal and to introduce the modulated signal to the monitor means;

means responsive in the monitor means to the disposition of the transducer assembly out of proximity to the heart rate of the fetus for retaining for at least a particular period of time the last indications provided by the monitor means of the fetal heart rate;

the rejecting means in the monitor means including means responsive to abrupt signals of large magnitude resulting from changes in the disposition of the transducer assembly unrelated to the heart rate of the fetus for inhibiting such signals from affecting the indications of fetal heart rate and means responsive in the monitor means to the disposition of the transducer assembly out of proximity with the heart of the fetus for retaining for at least a particular period of time the last indication provided by the monitor means of the fetal heart rate; and means for restoring the last indications provided by the monitor means of the fetal heart rate when the transducer assembly is returned in proximity to the heart rate of the fetus.

13. Apparatus for monitoring the heart rate of a fetus in an expectant mother, comprising:

a housing;

a first ultrasonic transducer included in the housing and constructed to be disposed externally of the abdomen of the expectant mother to transmit signals at a particular frequency to the fetus;

a second ultrasonic transducer included in the housing and constructed to be disposed externally on the abdomen of the expectant mother to receive from the fetus the signals at the particular frequency but modulated by the heart rate of the fetus;

an ultrasonic transducer assembly, including the first and second transducers, constructed to provide for the transmission of the signals at the particular frequency to the fetus and to receive the modulated signals from the fetus;

the transducer assembly including means included in the housing for matching the impedance of the first transducer to the impedance of the abdomen of the expectant mother and means for matching the impedance of the second transducer to the impedance of the abdomen of the expectant mother;

monitor means responsive to the modulated characteristics of the received signal to detect such modulations for the production of indications representing the heart rate of the fetus, the monitor means including means for passing the modulations and rejecting artifact noise;

coupling means releasably connecting the transducer assembly with the monitor means to introduce the modulated signals to the monitor means;

means for providing a carrier signal having a particular frequency;

means for modulating the carrier signals with the signals passing through the monitor means and for transmitting the signals to a distant position;

means at the distant position for demodulating the signals transmitted to the distant position;

means responsive to a change in the disposition of the transducer assembly means to a position removed from the heart of the fetus for providing for at least a particular period of time a signal having a frequency representing the last rate of the heart beat of the fetus before such change in disposition; and means responsive to a restoration of the transducer assembly means on the abdomen of the expectant mother for restoring the signal having the last rate of the heart beat.

* * * * *